United States Patent [19]

Metcalf et al.

[11] 4,293,548

[45] Oct. 6, 1981

[54] 18-SUBSTITUTED PREGN-4-ENE-3,20-DIONES

[75] Inventors: Brian W. Metcalf, Mason; J. O'Neal Johnston, Cincinnati, both of Ohio

[73] Assignee: Merrell Dow Pharmaceuticals Inc., Cincinnati, Ohio

[21] Appl. No.: 183,534

[22] Filed: Sep. 2, 1980

[51] Int. Cl.$^3$ .......................... C07J 5/00; A61K 31/56
[52] U.S. Cl. ........................... 424/242; 260/239.55 C; 260/397.47; 260/397.3; 260/397.45; 424/243
[58] Field of Search .................. 260/397.45, 239.55 R, 260/397.47; /Steroids MS File

[56] References Cited

U.S. PATENT DOCUMENTS 3,796,728  3/1974  Tanabe ............................. 260/345.9
3,842,074 10/1974  Anner et al. ............... 260/239.55 C
4,052,421 10/1977  Biollaz et al. .................... 260/397.4

OTHER PUBLICATIONS

R. Van Moorselaar et al., "Rec. Trav. Chim. Pays-–Bas," 88 (1969) pp. 737–751.

Primary Examiner—Elbert L. Roberts
Attorney, Agent, or Firm—John J. Kolano; Raymond A. McDonald; William J. Stein

[57] ABSTRACT

Progesterone derivatives having a vinylidene or a 1-alkynyl substituent at the 18-position and further optionally hydroxylated at the 11-position and the 21-position are described herein. Compounds having both an ethynyl substituent and a hydroxy substituent at the 18-position are also described herein. The compounds are useful as aldosterone inhibitors.

16 Claims, No Drawings

18-SUBSTITUTED PREGN-4-ENE-3,20-DIONES

BACKGROUND OF THE INVENTION

Aldosterone is a steroidal hormone which is synthesized in the zona glomerulosa cells of the adrenal glands. The primary biological function of this compound is the regulation of salt retention and, in particular, aldosterone plays a major role in controlling the reabsorption of sodium ions from the urine by the kidney. Thus, a deficiency of the enzyme responsible for the synthesis of aldosterone is a characteristic of patients with a salt-losing syndrome, while primary hyperaldosteronism can result from hyperbiosynthesis of aldosterone as caused by an adrenocortical tumor or the administration of certain drugs. The hyperaldosteronism may involve hypertension, hypokalemia, alkalosis, muscular weakness, polyuria and polydipsia. Thus, treatment of hyperaldosteronism and the conditions associated with it would be possible by blockage of the enzymatic synthesis of aldosterone.

SUMMARY OF THE INVENTION

The present invention relates to aldosterone inhibitors which are progesterone derivatives having a vinylidene or a 1-alkynyl substituent at the 18-position or both an ethynyl and a hydroxy substituent at the 18-position and optionally having a hydroxy substituent at the 11-position and the 21-position.

DETAILED DESCRIPTION OF THE INVENTION

The present invention relates to compounds of the formula

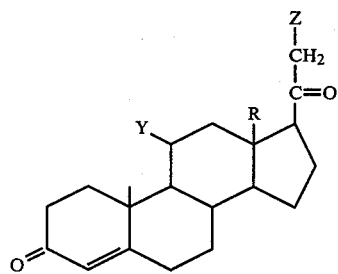

wherein Y is hydrogen or hydroxy; Z is hydrogen or hydroxy; and R is 1,2-propadienyl, 2-alkynyl containing up to 6 carbon atoms, or 1-hydroxy-2-propynyl. The propadienyl group can also be called allenyl and has the following structure:

Since the carbon with the free valence would also be the 18-carbon of a pregnane skeleton in the compounds of the present invention, such compounds can also be considered as 18-vinylidenepregnanes. The 2-alkynyl group has a triple bond at the second carbon with respect to the free valence and can be illustrated by the following structure:

wherein R' is hydrogen or alkyl containing up to three carbon atoms. Examples of 2-alkynyl groups are 2-propynyl, 2-butynyl, 2-pentynyl or 2-hexynyl although 2-propynyl is preferred. The 1-hydroxy-2-propynyl group has the following structure:

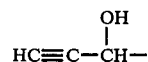

The compounds of the present invention can be prepared from an appropriate pregnan-18-al. The 3- and 20-carbonyl groups ordinarily present in the starting materials used are usually protected as the ketal, preferably that obtained using ethylene glycol. More specifically, the protected compounds involved can be obtained by treatment of the appropriate pregnan-3,20-dione with ethylene glycol in the presence of a trace of acid. Alternatively, it may be possible to protect the 3-position by reduction of the 3-ketone to the alcohol with lithium aluminum hydride followed by reaction with t-butyl dimethylsilyl chloride to give the corresponding ether. Any hydroxy groups present can be protected as the corresponding acetyl ester although it should be noted that any compound containing an 11-hydroxy group can exist in the form of an acetal with the 18-oxo group.

The propadienyl compounds can be obtained from the indicated pregnan-18-al by a series of reactions which can be illustrated as follows:

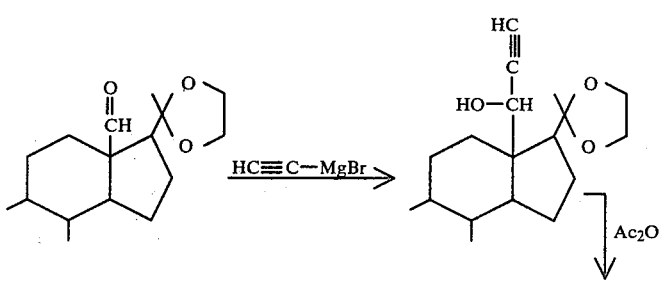

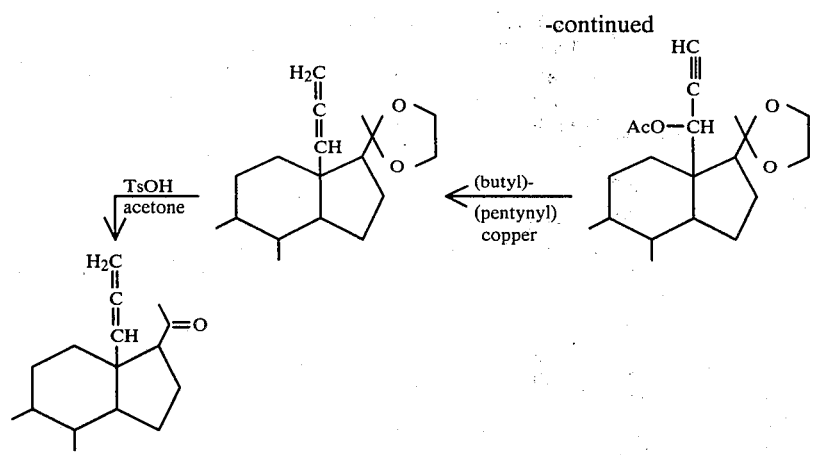

The above example only shows the C- and D-rings of the steroid in a compound without any hydroxy substituents. Specifically, the 18-al is reacted with ethynylmagnesium bromide to give the corresponding 13-(1-hydroxy-2-propynyl) compound. This is then converted to the corresponding ester using an anhydride such as acetic anhydride and treatment of the ester with lithium (butyl)(1-pentynyl)cuprate gives the corresponding 13-(propadienyl)compound. Any protecting groups, such as the 20-ketal group, are then removed by standard procedures such as treatment with p-toluenesulfonic acid and acetone or hydrogen chloride in aqueous methanol to give the desired propadienyl products. The protecting ketal group can also be removed in a similar manner from the 13-(1-hydroxy-2-propynyl) compounds described earlier as intermediates and this gives the compounds of the present invention having that same substitution at the 13-position.

To obtain the 13-(2-propynyl)-compounds, the 18-carboxaldehyde is used in the following series of reactions:

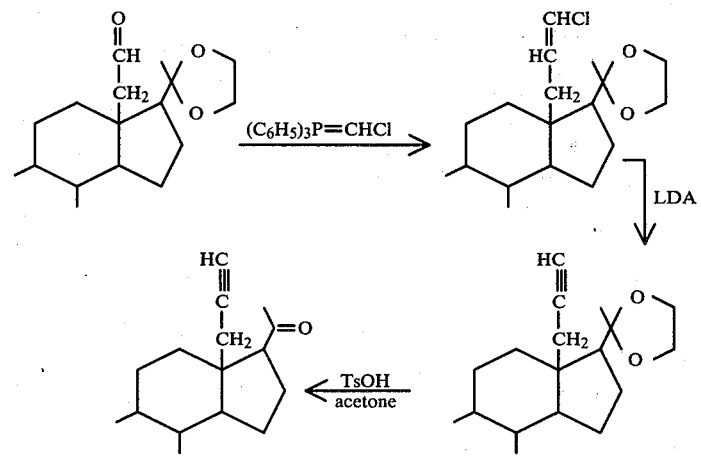

Again, only the C- and D-rings of a simple molecule are shown. The indicated 18-carboxaldehyde can be obtained from the corresponding nitrile by reduction with diisobutylaluminum hydride or it can be obtained from the 18-al referred to earlier by reaction with (methoxymethylene)triphenylphosphorane followed by Hg++ catalyzed hydrolysis. The 18-carboxaldehyde is reacted with (chloromethylene)triphenylphosphorane to give the corresponding 13-(3-chloro-2-propenyl)-compound as a mixture of cis- and trans-isomers. The chloro-compound is then dehydrohalogenated using a strong base such as lithium diisopropylamide or lithium amide in ammonia to give the propynyl compound and any protecting ketal groups are finally removed by standard procedures such as treatment with p-toluenesulfonic acid in the presence of acetone.

While certain of the procedures above can be used, with some modification, to give the corresponding compounds with a 21-hydroxy group, it is also possible to obtain such compounds by carrying out further reactions on the products described earlier. Specifically, in the propadienyl series, the 3-ketone is reacted with pyrrolidine in methanol (after conversion of any 11-hydroxy group to the acetate ester) to give the 3-(1-pyrrolidinyl)-3,5-diene which is then treated with lead tetraacetate to introduce an acetoxy group at the 21-position. The ester group or groups are then hydrolyzed with a base such as sodium hydroxide to give the desired product.

In the case of the 13-(2-propynyl)-compound without an 11-hydroxy group, the 21-oxygen group is introduced in a similar manner although the oxygen at the 3-position is protected in a different manner. That is, by reduction of the 3,20-diketone followed by selective oxidation and ketalization of the 3-ketone and oxidation of the 20-hydroxy group, there is obtained 3,3-ethylenedioxy-18-ethynylpregn-5-en-20-one which is then treated with lead tetraacetate and then base in the manner described earlier.

For the preparation of the 11β-hydroxy-13-(2-propynyl)compound, it is possible to obtain 11β,21-diacetoxy-3,3,20,20-bis(ethylenedioxy)pregn-5-en-18-al by a series of reactions from 11β-hydroxypregn-4-ene-3,20-dione and then convert the 18-al to a 2-propynyl-group by the series of reactions described earlier for such a conversion.

The present compounds are aldosterone inhibitors, i.e., they inhibit the synthesis of aldosterone. They are thus useful in the treatment of hyperaldosteronism and various conditions wherein a reduction of the excessive amount of aldosterone responsible for the condition would be beneficial. More specifically, they are useful in the general treatment of hyperaldosteronism and any associated edema and/or sodium retention whether this is the result of some bodily disorder or whether it results from the administration of some agent. As a result of their effect on the factors responsible for edema and/or sodium retention, the present compounds would be useful as diuretic agents.

The activity of the present compounds as aldosterone inhibitors can be demonstrated by the following procedure which measures the inhibition of enzymes in the synthesis of aldosterone.

Bovine adrenocortical mitochondrial fractions were prepared by differential centrifugation and used as a source of adrenal steroid hydroxylases. Enzyme incubation medium contained 8.5 mM $MgCl_2$, 2.7 mM $CaCl$, 3.13 mM KCl, 7.59 mM NaCl and buffered to pH 7.0 with 10 mM phosphate buffer. A NADPH generation system is included which uses 0.5 mM $NADP^+$, 2.5 mM glucose-6-phosphate and 1.0 unit of glucose-6-phosphate dehydrogenase in assay buffer.

Tritium-labeled desoxycorticosterone or corticosterone (40–60 Ci/mM specific activity) are dissolved in assay buffer to provide an assay concentration of 1 μCi in 100 μl of buffer. Compounds to be tested as enzyme inhibitors are solubilized in either ethanol or dimethylsulfoxide and diluted with buffer to provide assay concentrations varying from $10^{-4}$ to $10^{-9}$ M.

Test compounds are evaluated for time-dependent enzyme inhibition. The compound in 100 μl of buffer is added to 35 ml centrifuge tubes containing 600 μl of NADPH generating system. The preincubation is started by the addition of 700 μl of mitochondrial fraction (usually 2–4 mg protein/ml). These components are mixed and preincubated in a Dubnoff metabolic shaker for 0, 10, 20 or 40 minutes at 37° C. under an atmosphere of 95:5, $O_2:CO_2$. Following the preincubation period, 100 μl of the tritium labeled substrate at a concentration of at least 3 times the Km of the enzyme is added to the assay tubes. The incubation is continued for an additional 10 minutes. The enzyme reaction is stopped by the addition of 10 ml of methanol:chloroform, (1:1 v/v). Non-radiolabeled carrier desoxycorticosterone, corticosterone, 18-hydroxy-corticosterone and aldosterone are added. The chloroform phase is removed, evaporated to dryness, dissolved in 50 μl of chloroform and applied to silica gel TLC plate. Following standard chromatographic procedures the steroid spots are localized via UV illumination. Each TLC spot is transferred to a liquid scintillation vial, the steroid solubilized from the silica with ethanol prior to the addition of liquid scintillation counting cocktail. The radioactivity of the enzyme products is measured by β-scintillation spectrometer and the extent of inhibition of aldosterone synthesis is calculated therefrom.

Desoxycorticosterone is used as the substrate in assays to specifically evaluate the effects of inhibitors on 11β-hydroxylase system. Substrates for the 18-oxygenase system are corticosterone for 18-hydroxylase and 18-hydroxycorticosterone for the 18-hydroxydehydrogenase.

To achieve a desired effect, such as a diuretic effect, the compounds of the present invention can be administered orally, parenterally, for example, intramuscularly and subcutaneously, to a patient in need of treatment. The term patient is taken to mean a warm-blooded mammal, animals, rats, mice, dogs, cats, horses, pigs, cows, sheep and humans. The compounds of the invention can be administered alone or suitably admixed in the form of a pharmaceutical preparation to the patient being treated. The amount of compound administered will vary with the severity of the condition and repetitive treatment may be desired. For oral and parenteral administration the amount of compound administered, that is, the diuretic effective amount, is from 0.1 to 150 mg/kg of body weight per day and preferably from 1 to 50 mg/kg of body weight per day. Unit dosages for oral or parenteral administration may contain, for example, from 5 to 200 mg of the active ingredient. The compounds can be administered alone or in combination with one another.

For oral administration the compounds can be formulated into solid or liquid preparations, such as, capsules, pills, tablets, troches, powders, solutions, suspensions or emulsions. The solid unit dosage forms can be a capsule which can be of the ordinary gelatin type containing the active compound and a carrier, for example, lubricants and inert filler such as lactose, sucrose and corn starch. In another embodiment, an active compound of the invention can be tableted with conventional tablet bases such as lactose, sucrose and corn starch in combination with binders such as acacia, corn starch or gelatin, disintegrating agents such as potato starch or alginic acids and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanols and glycols, such as, propylene glycol or polyethylene glycol are preferred liquid carriers, particularly for injectable solutions.

The compounds can be administered in the form of a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic, silicone rubber manufactured by the Dow-Corning Corporation.

The following are illustrative pharmaceutical formulations suitable for oral or parenteral administration which may be employed in practicing the present invention:

TABLET

| | | |
|---|---|---|
| (a) | 18-Ethynyl-21-hydroxypregn-4-ene-3,20-dione | 75 g |
| (b) | Lactose | 1.216 Kg |
| (c) | Corn starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| | |
|---|---|
| (a) Magnesium Stearate | 0.015 Kg |
| (b) Corn starch qs ad | 1.725 Kg |

Compress on a suitable tablet machine to a weight of 0.115 g/tablet.

SOFT GELATIN CAPSULE

| | | |
|---|---|---|
| (a) | 18-Ethynyl-21-hydroxypregn-4-ene-3,20-dione. | 0.25 Kg |
| (b) | Polysorbate 80 | 0.25 Kg |
| (c) | Corn oil qs ad | 25.0 Kg |

Mix and fill into 50,000 soft gelatin capsules.

IM DEPOT INJECTION

Each 1 ml contains the following:

| | | |
|---|---|---|
| (a) | 18-Ethynyl-21-hydroxypregn-4-ene-3,20-dione | 5.0 mg |
| (b) | Anhydrous chlorobutanol | 5.0 mg |
| (c) | Aluminum monostearate | 50.0 mg |
| (d) | Peanut oil qs ad | 1.0 ml |

Dissolve or disperse the ingredients in the peanut oil.

DEPOT-IMPLANT

| | | |
|---|---|---|
| (a) | 18-Ethynyl-21-hydroxypren-4-ene-3,20-dione | 5.0 mg |
| (b) | Dimethylsiloxane | 240.0 mg |
| (c) | Catalyst qs | |

Disperse the drug substance in the fluid dimethylsiloxane. Add the catalyst and cast into a suitable monolytic structure.

Alternatively, the drug substance may be enclosed by a precast, polydimethylsiloxane envelope.

Alternatively, the drug substance may be dispersed in a suitable amount of hydroxyethyl acrylate subsequently polymerized and cross-linked by the addition of ethylenedimethacrylate, and an oxidizing agent, to yield a 3-dimensional ethylene glycomethacrylate moldable gel (Hydron).

| IM INJECTIONS | | |
|---|---|---|
| OIL TYPE: | | |
| (a) | 18-Ethynyl-21-hydroxypregn-4-ene-3,20-dione | 25 mg |
| (b) | BHA, BHT aa | 0.01% w/v |
| (c) | Peanut oil or sesame oil qs | 1.0 ml |

| -continued | | |
|---|---|---|
| B. SUSPENSION TYPE: | | |
| (a) | 18-Ethynyl-21-hydroxypregn-4-ene-3,20-dione | 25 mg |
| (b) | Sodium carboxymethylcellulose | 0.5% w/v |
| (c) | Sodium bisulfite | 0.02% w/v |
| (d) | Water for injection, qs | 1.0 ml |
| BUCCAL OR SUBLINGUAL TABLET | | |
| (a) | 18-Ethynyl-21-hydroxypregn-4-ene-3,20-dione | 1% |
| (b) | Calcium stearate | 1% |
| (c) | Calcium saccharin | 0.02% |
| (d) | Granular mannitol | qs |

Mix and compress on a suitable tablet machine to a weight of 0.115 g/tablet.

The following specific examples are presented to illustrate the present invention and should not be construed as limiting it in any way. In the examples, all temperatures are set forth uncorrected in degrees Celsius; unless otherwise indicated, all parts and percentages are by weight.

Where the description of a particular process step is provided in general terms, the procedure is based on a widely known reaction and it is essentially the same as the described in detail elsewhere in the examples. Thus, the conversion of ketones to ketals is described in Examples 3 and 10 while the conversion of a ketal back to a ketone is described in Example 1. The alkaline hydrolysis of (acetate) esters is described in detail in Example 6, while Example 10 provides a description of a pyridinium chlorochromate oxidation [E. J. Corey and J. W. Suggs, *Tetrahedron Letters*, 31, 2647 (1975)]. Example 1 also contains a description of the preparation and use of lithium (butyl)(1-pentynyl)cuprate [P. Baret et al., *Tetrahedron*, 35, 2931, (1979)].

EXAMPLE 1

A solution of 3.0 g of 3,3,20,20-bis(ethylenedioxy)-pregn-5-en-18-al in 35 ml of tetrahydrofuran is cooled to 0° C. and a solution of 7.2 mmoles of ethynylmagnesium bromide in tetrahydrofuran is added dropwise. When the addition is complete, the mixture is heated at reflux for 1 hour, cooled and diluted with ether and the resulting solution is poured into an ice-cooled saturated aqueous solution of ammonium chloride. The organic layer is separated, washed thoroughly with water and with brine and dried and the solvent is evaporated. The residue is chromatographed on silica gel using hexane/ethyl acetate to give 3,3,20,20-bis(ethylenedioxy)-18-ethynylpregn-5-en-18-ol.

The 18-hydroxy compound obtained above (2.2 g) is dissolved in 25 ml of pyridine and then cooled to 0° C. Acetic anhydride (610 mg) is added and the mixture is allowed to warm slowly to room temperature overnight. It is then diluted with ether and washed with 1 N hydrochloric acid, saturated sodium bicarbonate and brine and then dried. The solvent is evaporated and the residue is dried thoroughly under high vacuum to give 18-acetoxy-3,3,20,20-bis (ethylenedioxy)-18-ethynyl-pregn-5-ene which is used directly in the next step.

To a suspension of 6.6 g of 1-pentynyl copper in 110 ml of ether there is added n-butyllithium (23 ml of a 2.2 M hexane solution) at −40° C. The resulting slurry of lithium (butyl)(1-pentynyl)cuprate is maintained at this temperature for 1 hour and then cooled to −70° C. A solution of the 18-acetoxy compound obtained in the preceding paragraph in 15 ml of ether is added. After 6 minutes at −70° C., 2 ml of methanol is added followed by saturated aqueous ammonium chloride solution. The mixture is then diluted with ether and filtered through Celite. The organic layer is then separated, washed with 1 N hydrochloric acid, and saturated aqueous sodium bicarbonate and then dried and concentrated. The resulting residue is chromatographed on silica gel using ethyl acetate/hexane to give 3,3,20,20-bis(ethylenedioxy)-18-vinylidenepregn-5-ene which is recrystallized from methylene chloride/hexane.

A solution of 1.1 g of the 18-vinylidene compound obtained above in 15 ml of acetone is treated with a catalytic amount of p-toluenesulfonic acid overnight at room temperature. The resulting solution is concentrated and the residue is dissolved in ether. The ether solution is washed with saturated aqueous sodium bicarbonate and with brine and dried, and the solvent is evaporated. The residue is purified by chromatography on silica gel using ethyl acetate/hexane followed by recrystallization from methylene chloride/hexane to give 18-vinylidenepregn-4-ene-3,20-dione. This compound has the following structural formula:

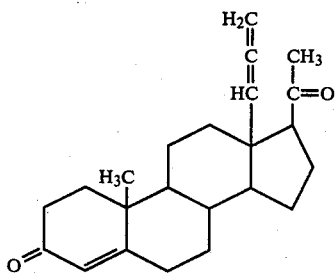

EXAMPLE 2

A solution is prepared from 3.3 g of 18-vinylidenepregn-4-ene-3,20-dione in the minimum amount of hot methanol and 700 mg of pyrrolidine is added to the hot solution. When the product begins to crystallize, the mixture is chilled rapidly in ice water. The mixture is diluted with methanol and the solid is separated by filtration and dried under high vacuum to give 3-(1-pyrrolidinyl)-18-vinylidenepregna-3,5-dien-20-one which is used in the next step without further purification.

The pyrrolidinyl compound obtained above is treated with 4.9 g of lead tetraacetate in 50 ml of glacial acetic acid at 70° C. for 24 hours. The mixture is then cooled and diluted with ether and filtered through Celite. The filtrate is washed thoroughly with water and saturated aqueous sodium bicarbonate and dried and concentrated. The crude product is then saponified using 5% sodium hydroxide in methanol. The product obtained is purified by chromatography on silica gel using ethyl acetate/hexane followed by recrystallization to give 21-hydroxy-18-vinylidenepregn-4-ene-3,20-dione. This compound has the following structural formula:

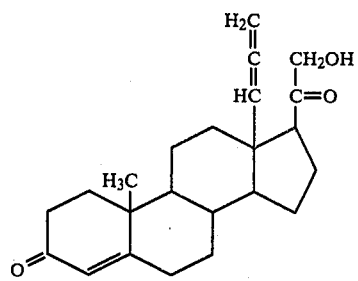

EXAMPLE 3

A mixture of 3.5 g of 18-cyano-3,3-ethylenedioxypregn-5-ene-20-one, 2.8 g of ethylene glycol, 0.2 g of p-toluenesulfonic acid and 45 ml of benzene is refluxed for 16 hours using a Dean-Stark water trap. The reaction mixture is then cooled, washed with aqueous saturated sodium carbonate, water and brine and then dried and the solvent is evaporated. The residual crude product is dissolved in anhydrous tetrahydrofuran and cooled to −70° C. Diisobutyl aluminum hydride (9.1 ml of a 1 M solution) is added dropwise and the solution is allowed to warm slowly to room temperature. The reaction mixture is then diluted with ether and poured into aqueous 1 N hydrochloric acid. The ether layer is separated, washed with 1 N hydrochloric acid, sodium bicarbonate and brine and dried and the solvent is evaporated. The residue is purified by chromatography on silica gel and recrystallized to give 3,3,20,20-bis(ethylenedioxy)pregn-5-ene-18-carboxaldehyde.

A solution of lithium diisopropylamide is prepared from 0.67 g of diisopropylamine and 2.9 ml of 2.2 M hexane solution n-butyllithium in 10 ml of tetrahydrofuran and cooled to −70° C. and then added to a solution of 2.3 g of (chloromethyl)triphenylphosphonium chloride in 10 ml of tetrahydrofuran. To the resulting ylid [(chloromethylene)triphenylphosphorane] solution is added a solution of 2.8 g of 3,3,20,20-bis(ethylenedioxy)pregn-5-ene-18-carboxaldehyde in 10 ml of anhydrous tetrahydrofuran. The mixture is then allowed to warm to room temperature before it is quenched with water and extracted with ether. The ether extract is dried and concentrated and the product is purified by chromatography on silica gel to give 18-(2-chloroethenyl)-3,3,20,20-bis(ethylenedioxy)pregn-5-ene as a mixture of cis and trans isomers.

A solution of lithium diisopropylamide is prepared from 0.3 g of diisopropylamine and n-butyllithium in 10 ml of tetrahydrofuran at −70° C. and to this cold solution is added a solution of 1.5 g of the 2-chloroethenyl compound obtained above in 5 ml of tetrahydrofuran. The mixture is stirred at −70° C. for 1.5 hours and then quenched by the addition of saturated aqueous ammonium chloride. The mixture is extracted with ether and the ether extract is washed with 1 N hydrochloric acid, saturated aqueous sodium bicarbonate and brine. It is then dried and the solvent is evaporated. The residual crude 3,3,20,20-bis(ethylenedioxy)-18-ethynylpregn-5-ene is dissolved in 25 ml of acetone, a catalytic amount of p-toluenesulfonic acid is added and the mixture is stirred overnight at room temperature. The acetone is then evaporated and the residue is dissolved in chloroform. The chloroform solution is washed with saturated sodium bicarbonate solution and dried and the solvent is evaporated. The residue obtained is chromatographed on silica gel using ethyl acetate/hexane to give 18-ethynylpregn-4-ene-3,20-dione which is further purified by recrystallization from methylene chloride/hexane. This compound has the following structural formula:

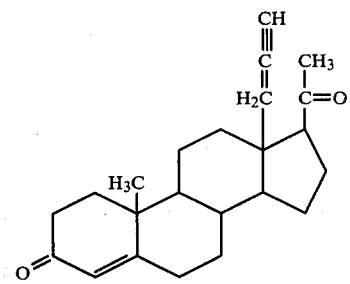

EXAMPLE 4

A solution of 4.2 g of 18-ethynylpregn-4-ene-3,20-dione in 125 ml of methanol is cooled to 0° C. and 950 mg of sodium borohydride is added. The resulting mixture is stirred at 0° C. for 1 hour and then allowed to warm to room temperature over an additional hour. Acetic acid is then added and the solution is concentrated. The resulting residue is suspended in ethyl acetate, washed with water, aqueous sodium bicarbonate and brine and dried, and the solvent is evaporated. The residue is dissolved in 400 ml of chloroform, 42 g of activated manganese dioxide is added, and the resulting suspension is stirred for 24 hours. The inorganic solid is then removed by filtration through Celite and the filter cake is washed thoroughly with hot chloroform. The filtrate is then concentrated and the residue is purified by recrystallization from acetone/hexane to give 18-ethynyl-20-hydroxypregn-4-en-3-one.

This compound is treated first with ethylene glycol and p-toluenesulfonic acid in benzene and then oxidized with pyridinium chlorochromate to give 3,3-ethylenedioxy-18-ethynylpregn-5-en-20-one.

A mixture of 3.8 g of 3,3-ethylenedioxy-18-ethynylpregn-5-en-20-one and 4.4 g of lead tetraacetate in 50 ml of acetic acid is heated at 70° C. for 24 hours. The mixture is then cooled and poured into water and then extracted with ether. The ether extract is washed with water, aqueous sodium bicarbonate and brine and then dried and concentrated. The residue is chromatographed on silica gel using ethyl acetate/hexane to give 21-acetoxy-3,3-ethylenedioxy-18-ethynylpregn-5-en-20-one.

The above product is treated first with acetone and p-toluenesulfonic acid and then with sodium hydroxide in ethanol to give 18-ethynyl-21-hydroxypregn-4-ene-3,20-dione. This compound has the following structural formula:

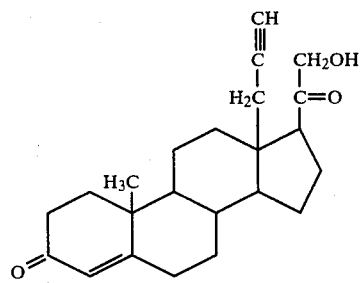

EXAMPLE 5

A solution of 5 g of 3,3,20,20-bis(ethylenedioxy)-11β-hydroxypregn-5-en-18-al in 15 ml of tetrahydrofurn is added dropwise to a solution of 2 equivalents of ethynylmagnesium bromide in 45 ml of tetrahydrofuran at 0° C. After the addition is complete, the mixture is allowed to warm to room temperature over a period of 2 hours. The mixture is then quenched by pouring in into ice-cold 0.5 N hydrochloric acid. The resulting mixture is extracted with ether and the extract washed with aqueous sodium bicarbonate and brine and then dried and concentrated. The residue is chromatographed on silica gel using methylene chloride/methanol to give 3,3,20,20-bis(ethylenedioxy)-18-ethynylpregn-5-ene-11β,18-diol.

A solution of 3.1 g of the diol obtained above in 65 ml of pyridine is cooled to 0° C. and 1.5 g of acetic anhydride is added dropwise. The resulting solution is allowed to warm slowly and is stirred for 16 hours. Methanol (1 ml) is added and the solvent is evaporated under reduced pressure. The resulting residue is dissolved in ether and washed with 1 N hydrochloric acid, aqueous sodium bicarbonate and brine. The ether solution is dried and concentrated and the residue obtained is recrystallized from aqueous ethanol to give 11β,18-diacetoxy-3,3,20,20-bis(ethylenedioxy)-18-ethynylpregn-5-ene.

Cuprate reagent prepared from 55 mmoles of n-butyllithium and 7.2 g of pentynyl copper is cooled at −70° C. and a solution of 3.0 g of the diacetoxy compound obtained above in 15 ml of ether is added. After 6 minutes at −70° C. the reaction mixture is quenched and worked up as above. The product is isolated by silica gel chromatography to give 11β-acetoxy-3,3,20,20-bis(ethylenedioxy)-18-vinylidenepregn-5-ene.

The 11β-acetoxy-3,3,20,20-bis(ethylenedioxy)-18-vinylidenepregn-5-ene obtained above is treated first with sodium hydroxide in ethanol and then with acetone in the presence of p-toluenesulfonic acid to give 11β-hydroxy-18-vinylidenepregn-4-ene-3,20-dione.

EXAMPLE 6

11β-Hydroxy-18-vinylidenepregn-4-ene-3,20-dione is acetylated with acetic anhydride in pyridine to give the corresponding 11β-acetate. The acetate (2.5 g) is treated with 0.45 g of pyrrolidine in methanol and heated briefly. The solution is then cooled rapidly and solid product crystallizes. This is separated by filtration and dried under high vacuum to give crude 11β-acetoxy-3-(1-pyrrolidinyl)-18-vinylidenepregn-3,5-dien-20-one which is used without further purification.

A mixture of the ene-amine from the above reaction with 2.8 g of lead tetraacetate and 50 ml of acetic acid is heated at 70° C. under argon for 18 hours. The mixture is then cooled, poured into water and extracted with methylene chloride. The extract is washed with water, dried and concentrated. The crude product is dissolved in 95% ethanol and saturated sodium bicarbonate is added. After stirring at room temperature for 2.5 hours, the solution is neutralized with 0.5 N hydrochloric acid and concentrated to a small volume. The residue is extracted with ether and the extract is washed with water, dried and concentrated. The residue is then chromatographed on silica gel to give 11β,21-diacetoxy-18-vinylidenepregn-4-ene-3,20-dione.

The diacetate obtained above (500 mg) is treated with a 5% solution of sodium hydroxide in ethanol at 0° C. for 2 hours. The solution is then neutralized with 0.5 N hydrochloric acid and concentrated. The residue obtained is dissolved in ethyl acetate, washed with aqueous sodium bicarbonate and brine and then dried and the solvent is evaporated. The crude residue obtained is recrystallized from ethyl acetate/hexane to give 11β,21-hydroxy-18-vinylidenepregn-4-ene-3,20-dione.

EXAMPLE 7

A solution of 4.0 g of (methoxymethyl)triphenylphosphonium chloride and 20 ml of tetrahydrofuran is added to lithium diisopropylamide prepared from 1.2 g of diisopropylamine and 5.3 ml of a 2.2 M solution of n-butyllithium in hexane all in 20 ml of tetrahydrofuran at −70° C. After stirring 10 minutes at that temperature, the 3,3,20,20-bis(ethylenedioxy)-11β-hydroxypregn-5-en-18-al (5 mmoles) in 20 ml of tetrahydrofuran is added. The cooling bath is then removed and the solution is allowed to warm to room temperature. The reaction mixture is then quenched by the addition of water and then diluted with ether. The ether layer is separated, washed with 1 N hydrochloric acid, aqueous sodium bicarbonate and brine, and then dried and concentrated. The residue is chromatographed on silica gel using ethyl acetate/hexane to give 3,3,20,20-bis(ethylenedioxy)-18-(methoxymethylene)pregn-5-en-11β-ol.

A solution is prepared from 6.7 g of mercuric acetate in the minimum amount of 10:1 tetrahydrofuran:water at room temperature and 3.3 g of the methoxymethylene compound obtained above is added. The mixture is stirred for 10 minutes, saturated aqueous potassium iodide solution is added and the solution is extracted with ethyl acetate. The extract is then washed with water, 10% aqueous sodium bisulfite and brine. The mixture is then dried and concentrated to give 3,3,20,20-bis(ethylenedioxy)-11β-hydroxypregn-5-ene-18-carboxaldehyde which is used in the next step without further purification.

The 18-carboxaldehyde obtained above is subjected to the Wittig reaction with two equivalents of (chloromethylene)triphenylphosphorane as described in Example 3. The crude product is chromatographed on silica gel using ethyl acetate/hexane to give 18-(2-chloroethenyl)-3,3,20,20-bis(ethylenedioxy)pregn-5-en-11β-ol.

Using the procedure described in Example 3, the chloroethenyl compound obtained above is reacted first with lithium diisopropylamide and then with acetone in the presence of p-toluenesulfonic acid to give 18-ethynyl-11β-hydroxypregn-4-ene-3,20-dione.

EXAMPLE 8

11β-Hydroxypregn-4-ene-3,20-dione is reacted with acetic anhydride to give the corresponding 11β-acetoxy compound which is then reduced with sodium borohydride to give 11β-acetoxypregn-5-ene-3β,20-diol. This diol is reacted with manganese dioxide to oxidize the 3-hydroxy group to a ketone and this is reacted with ethylene glycol in the presence of acid to give 11β-acetoxy-3,3-ethylenedioxypregn-5-en-20-ol. All of the steps in this conversion involve standard procedures which have been described in detail above for the preparation of related compounds.

A mixture of 21.7 g of lead tetraacetate and 9.8 g of calcium carbonate in 1000 ml of cyclohexane is heated at reflux under argon for 1 hour and then cooled. To the resulting suspension is added 8.2 g of 11β-acetoxy-3,3-ethylenedioxypregn-5-en-20-ol and 2.5 g of iodine and the resulting purple suspension is heated to reflux and irradiated with a 275 W sunlamp until the color of the iodine has faded (1–1.5 hours). The mixture is then cooled and filtered through Celite and the filtrate is washed with aqueous sodium bisulfite, water, aqueous sodium bicarbonate and brine. The organic solution is then dried and concentrated and the residue obtained is dissolved in acetone and treated with 10 ml of standard Jones reagent at 0° C. for 1 hour. Excess Jones reagent is destroyed by the addition of 2-propanol and the resulting mixture is filtered to remove the precipitated inorganic salts. The filtrate is then concentrated to a small volume and the residue is partitioned between ether and water. The aqueous solution is extracted with ether and the ether solutions are combined, washed with aqueous sodium bicarbonate, dried and concentrated. The residue is dissolved in water:dioxane (1:9, 700 ml) and 7.2 g of silver acetate is added. The mixture is stirred and heated rapidly to 60°–65° C. and then maintained at that temperature for 4 hours. The mixture is then cooled, filtered and concentrated. The residue is dissolved in ether, filtered again and concentrated. The resulting material is chromatographed on silica gel to give 11β-acetoxy-3,3-ethylenedioxy-18-hydroxypregn-5-en-20-one.

The product obtained above is treated with p-toluenesulfonic acid in acetone to remove the ethylenedioxy group. The product obtained is dissolved in 40 ml of acetic acid, 2.4 g of lead tetraacetate is added and the mixture is stirred at room temperature for 15 minutes. It is then poured into water and the aqueous mixture is extracted with ether. The ether extract is washed with aqueous sodium bicarbonate and brine and then dried and concentrated. The residual material is purified by chromatography on silica gel using ethyl acetate/hexane to give 11β,21-diacetoxy-18-hydroxypregn-4-ene-3,20-dione.

The product obtained above is first treated with ethylene glycol in the presence of p-toluenesulfonic acid to give the bis-ketal followed by oxidation with pyridiniumchlorochromate to give 11β,21-diacetoxy-3,3,20,20-bis(ethylenedioxy)pregn-5-en-18-al. Following the procedure of Example 7, this aldehyde is subjected to the Wittig reacting using the ylid obtained from (methoxymethyl)triphenylphosphonium chloride. The product is cleaved with mercuric acetate to give 11β,21-diacetoxy-3,3,20,20-bis(ethylenedioxy)pregn-5-ene-18-carboxaldehyde. The 18-carboxaldehyde is then treated with (chloromethylene)triphenylphosphorane to give the corresponding 18-(2-chloroethenyl) compound which is then dehydrohalogenated using 4 equivalents of lithium diisopropylamide to give 11β,21-diacetoxy-3,3,20,20-bis(ethylenedioxy)-18-ethynylpregn-5-ene.

The product from the above reaction is treated with ethanolic sodium hydroxide to hydrolyze the ester groups. The product is then treated with acetone and p-toluenesulfonic acid to remove the two ethylenedioxy groups. The resulting product is purified by chromatography on silica gel followed by recrystallization to give 18-ethynyl-11β,21-dihydroxypregn-4-ene-3,20-dione.

EXAMPLE 9

11β,21-Diacetoxy-3,3,20,20-bis(ethylenedioxy)pregn-5-en-18-al is treated with excess ethynylmagnesium bromide to give 3,3,20,20-bis(ethylenedioxy)-18-ethynylpregn-5-ene-11β,18,21-triol. The triol is treated with acetic anhydride to give the corresponding triacetate which is then reacted with lithium (butyl)(1-pentynyl)cuprate to give 11β,21-diacetoxy-3,3,20,20-bis(ethylenedioxy)-18-vinylidenepregn-5-ene. The ester groups are hydrolyzed by treatment with ethanolic sodium hydroxide followed by removal of the ketal groups by treatment with acetone and p-toluenesulfonic acid. The resulting product is purified by chromatography on silica gel using methylene chloride/methanol and then recrystallized to give 11β,21-dihydroxy-18-vinylidenepregn-4-ene-3,20-dione.

EXAMPLE 10

A mixture of 4.2 g of 21-acetoxy-18-hydroxypregn-4-ene-3,20-dione, 6.7 g of ethylene glycol and 0.21 g of p-toluenesulfonic acid in 100 ml of benzene is heated at reflux for 16 hours. The mixture is cooled and washed with saturated aqueous potassium carbonate, water and brine and then dried and concentrated to give crude 21-acetoxy-3,3,20,20-bis(ethylenedioxy)pregn-5-en-18-ol which was used without further purification.

A solution of 5.0 g of the bis-ketal obtained above and 25 ml of methylene chloride is treated with 3.5 g of pyridinium chlorochromate at 25° C. for 2.5 hours. Ether (125 ml) is added to the mixture and then decanted and the residue is rinsed with ether two additional times. The combined ether solutions are filtered through Florisil followed by concentration and purification by chromatography on silica gel to give 21-acetoxy-3,3,20,20-bis(ethylenedioxy)pregn-5-en-18-al.

A solution of 4.3 g of the above aldehyde in 50 ml of a 5% solution of sodium hydroxide in ethanol is allowed to stand at 0° C. for 2 hours. The mixture is then neutralized with 1 N hydrochloric acid, concentrated to a small volume under reduced pressure and diluted with water. This is extracted with chloroform and the solvent evaporated to give 3,3,20,20-bis(ethylenedioxy)-21-hydroxypregn-5-en-18-al which is purified by recrystallization from aqueous ethanol.

The 21-hydroxy compound obtained above is reacted with two equivalents of ethynylmagnesium bromide in tetrahydrofuran to give 3,3,20,20-bis(ethylenedioxy)-18-ethynylpregn-5-ene-18,21-diol. Reaction of the diol with acetic anhydride in the presence of pyridine gives 18,21-diacetoxy-3,3,20,20-bis(ethylenedioxy)-18-ethynylpregn-5-ene. The diacetate is then reacted with lithium (butyl)(1-pentynyl)cuprate in ether at −70° C. to give 21-acetoxy-3,3,20,20-bis(ethylenedioxy)-18-vinylidenepregn-5-ene.

The acetate ester is hydrolyzed by treatment with a 5% solution of sodium hydroxide in ethanol at 0° C. and the two ketal groups are cleaved by reaction with p-toluenesulfonic acid in acetone. The crude product obtained is purified by chromatography on silica gel followed by recrystallization to give 21-hydroxy-18-vinylidenepregn-4-ene-3,20-dione.

EXAMPLE 11

To a solution of 400 mg of 3,3,20,20-bis(ethylenedioxy)-18-ethynylpregn-5-ene in 4 ml of tetrahydrofuran at room temperature is added methyllithium (1.1 ml of a 1.0 M solution in ether). After 10 minutes, 200 mg of methyl iodide is added and the mixture is stirred at room temperature for about 8 hours. The mixture is then diluted with ether, washed with brine and dried and the solvent is evaporated to give a residue which is 18-(1-propynyl)-3,3,20,20-bis(ethylenedioxy)pregn-5-ene. The ethylenedioxy groups are then removed by treatment with acetone and a catalytic amount of p-toluenesulfonic acid to give 18-(1-propynyl)pregn-4-ene-3,20-dione.

EXAMPLE 12

3,3,20,20-Bis(ethylenedioxy)-18-ethynylpregn-5-en-18-ol, 3,3,20,20-bis(ethylenedioxy)-18-ethynylpregn-5-ene-11β,18-diol, 3,3,20,20-bis(ethylenedioxy)-18-ethynylpregn-5-ene-18,21-diol and 3,3,20,20-bis(ethylenedioxy)-18-ethynylpregn-5-ene-11β,18,21-triol are each treated with acetone and a catalytic amount of p-toluenesulfonic acid at room temperature to give, respectively, 18-ethynyl-18-hydroxypregn-5-ene-3,20-dione, 18-ethynyl-11β,18-dihydroxypregn-4-ene-3,20-dione, 18-ethynyl-18,21-dihydroxypregn-4-ene-3,20-dione and 18-ethynyl-11β,18,21-trihydroxypregn-4-ene-3,20-dione.

What is claimed is:

1. A compound of the formula:

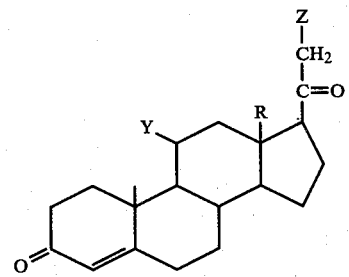

wherein Y is hydrogen or hydroxy; Z is hydrogen or hydroxy; and R is 1,2-propadienyl, 2-alkynyl containing up to 6 carbon atoms, or 1-hydroxy-2-propynyl.

2. A compound according to claim 1 which has the formula:

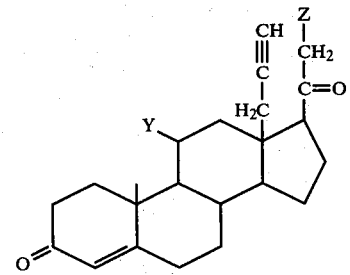

wherein Y is hydrogen or hydroxy and Z is hydrogen or hydroxy.

3. A compound according to claim 1 which is 18-ethynylpregn-4-ene-3,20-dione.

4. A compound according to claim 1 which is 18-ethynyl-21-hydroxypregn-4-ene-3,20-dione.

5. A compound according to claim 1 which is 18-ethynyl-11β-hydroxypregn-4-ene-3,20-dione.

6. A compound according to claim 1 which is 18-ethynyl-11β,21-dihydroxypregn-4-ene-3,20-dione.

7. A compound according to claim 1 which is 18-vinylidenepregn-4-ene-3,20-dione.

8. A compound according to claim 1 which is 21-hydroxy-18-vinylidenepregn-4-ene-3,20-dione.

9. A compound according to claim 1 which is 11β-hydroxy-18-vinylidenepregn-4-ene-3,20-dione.

10. A compound according to claim 1 which is 11β,21-dihydroxy-18-vinylidenepregn-4-ene-3,20-dione.

11. A compound according to claim 1 which is 18-ethynyl-18-hydroxypregn-4-ene-3,20-dione.

12. A compound according to claim 1 which is 18-ethynyl-11β,18-dihydroxypregn-4-ene-3,20-dione.

13. A process for preparing a compound of the formula

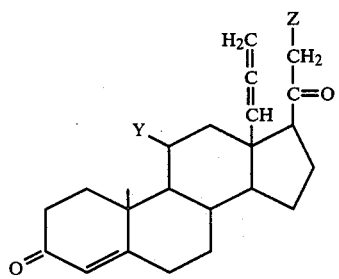

wherein Y is hydrogen or hydroxy and Z is hydrogen or hydroxy which comprises (a) reacting an appropriate 13-(1-acetoxy-2-propynyl)-steroid with lithium (butyl)(1-pentynyl)-cuprate to give a 13-allenyl group, (b) followed by the removal of any ketal protecting groups by treatment with acid and removal of any ester protecting groups by alkaline hydrolysis.

14. A process for preparing a compound of the formula

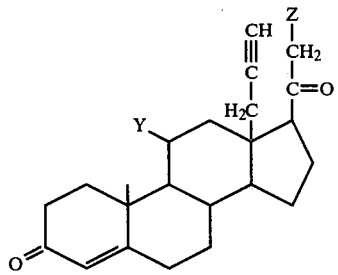

wherein Y is hydrogen or hydroxy and Z is hydrogen or hydroxy which comprises (a) reacting an appropriate 13-(3-chloro-2-propenyl)-steroid with a strong base to give a 13-(2-propynyl) group, (b) followed by the removal of any ketal protecting groups by treatment with acid and removal of any ester protecting groups by alkaline hydrolysis.

15. A method for treating hyperaldosteronism which comprises administering to a patient having said condition a therapeutically effective amount of a compound of claim 1.

16. A method for producing a diuretic effect which comprises administering to a patient in need of such treatment an effective amount of a compound of claim 1.

* * * * *

UNITED STATES PATENT AND TRADEMARK OFFICE
CERTIFICATE OF CORRECTION

PATENT NO. : 4,293,548
DATED : October 6, 1981
INVENTOR(S) : Brian W. Metcalf and J. O'Neal Johnston It is certified that error appears in the above-identified patent and that said Letters Patent are hereby corrected as shown below:

Column 9, line 24, "slica" should read -- silica --.
Column 11, lines 10-19, in the structural formula,

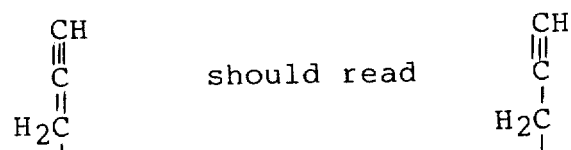

Column 12, line 17, "tetrahydrofurn" should read -- tetrahydrofuran --.
Column 16, line 27, "-hydroxypregn-5-ene-" should read -- -hydroxypregn-4-ene- --.

Signed and Sealed this

Third Day of January 1984

[SEAL]

Attest:

GERALD J. MOSSINGHOFF

Attesting Officer     Commissioner of Patents and Trademarks